United States Patent
Thibault et al.

(10) Patent No.: US 9,466,136 B2
(45) Date of Patent: Oct. 11, 2016

(54) METHODS AND SYSTEMS FOR PERFORMING MODEL-BASED IMAGE PROCESSING

(71) Applicant: General Electric Company, Schenectady, NY (US)

(72) Inventors: Jean-Baptiste Thibault, Waukesha, WI (US); Ruoqiao Zhang, W. Lafayette, IN (US); Charles Bouman, W. Lafayette, IN (US); Ken Sauer, Notre Dame, IN (US)

(73) Assignee: General Electric Company, Schenectady, NY (US)

( * ) Notice: Subject to any disclaimer, the term of this patent is extended or adjusted under 35 U.S.C. 154(b) by 314 days.

(21) Appl. No.: 14/092,383

(22) Filed: Nov. 27, 2013

(65) Prior Publication Data
US 2015/0146845 A1 May 28, 2015

(51) Int. Cl.
G06K 9/00 (2006.01)
G06T 11/00 (2006.01)
A61B 6/00 (2006.01)
A61B 6/03 (2006.01)

(52) U.S. Cl.
CPC .............. *G06T 11/006* (2013.01); *A61B 6/032* (2013.01); *A61B 6/5205* (2013.01)

(58) Field of Classification Search
None
See application file for complete search history.

(56) References Cited

U.S. PATENT DOCUMENTS

| | | | | |
|---|---|---|---|---|
| 6,249,594 B1* | 6/2001 | Hibbard | ............... | G06T 7/0012 382/128 |
| 7,929,775 B2* | 4/2011 | Hager | ............... | G06K 9/00208 382/154 |
| 8,798,373 B2* | 8/2014 | Shibata | ............... | G06T 5/005 382/195 |
| 2012/0294414 A1* | 11/2012 | Koehler | ............... | A61B 6/032 378/16 |

OTHER PUBLICATIONS

J. Besag, "Spatial interaction and the statistical analysis of lattice systems", Journal of the Royal Statistical Society. Series B (Methodological), pp. 192-236, 1974.
C. A. Bouman and K. D. Sauer, "A generalized Gaussian image model for edge-preserving MAP estimation", IEEE Transaction on Image Processing., vol. 2, pp. 296-310, Jul. 1993.
J.-B. Thibault, K. D. Sauer, J. Hsieh, and C. A. Bouman, "A three-dimensional statistical approach to improve image quality for multislice helical CT", Medical Physics, vol. 34, No. 11, pp. 4526-4544, Nov. 2007.
C. A. Bouman, "Cluster: An unsupervised algorithm for modeling Gaussian mixtures". Available from http://engineering.purdue.edu/~bouman, Apr. 1997.
E. Haneda and C. A. Bouman, "Implicit priors for model based inversion", technical report, Purdue ECE, Oct. 2011.
M. Elad and M. Aharon, "Image denoising via sparse and redundant representations over learned dictionaries", IEEE Transaction on Image Processing, vol. 15, No. 12, pp. 3736-3745, 2006.

(Continued)

*Primary Examiner* — Nancy Bitar
(74) *Attorney, Agent, or Firm* — Dean D. Small; The Small Patent Law Group, LLC.

(57) ABSTRACT

Methods and systems for model-based image processing are provided. One method includes selecting at least one reference image from a plurality of reference images, partitioning the at least one reference image into a plurality of patches, generating a probability distribution for each of the patches, and generating a model of a probability distribution for the at least one reference image using the probability distributions for each of the patches.

24 Claims, 6 Drawing Sheets

(56) References Cited

OTHER PUBLICATIONS

S. Roth and M. J. Black, "Fields of experts: A framework for learning image priors", Computer Vision and Pattern Recognition, 2005. CVPR 2005. IEEE Computer Society Conference on, vol. 2, 2005, pp. 860-867.

A. Buades, B. Coll, and J.-M. Morel, "A non-local algorithm for image denoising", Computer Vision and Pattern Recognition, 2005. CVPR 2005. IEEE Computer Society Conference on, vol. 2, 2005, pp. 60-65.

J. Portilla, V. Strela, M. J. Wainwright, and E. P. Simoncelli, "Image denoising using scale mixtures of Gaussians in the wavelet domain", IEEE Transaction on Image Processing, vol. 12, No. 11, pp. 1338-1351, 2003.

J. Guerrero-Colon, E. P. Simoncelli, and J. Portilla, "Image denoising using mixtures of Gaussian scale mixtures", Image Processing, 2008. ICIP 2008. 15th IEEE International Conference on, pp. 565-568.

H. Takeda, S. Farsiu, and P. Milanfar. "Kernel regression for image processing and reconstruction", IEEE Transaction on Image Processing, vol. 16, No. 2, pp. 349-366, 2007.

P. Chatterjee and P. Milanfar, "Clustering-based denoising with locally learned dictionaries", IEEE Transaction on Image Processing, vol. 18, pp. 1438-1451, 2008.

K. Dabov, A. Foi, V. Katkovnik, and K. Egiazarian, "Image denoising by sparse 3D transform-domain collaborative filtering", vol. 16, No. 8, pp. 2080-2095, 2007.

D. Zoran and Y. Weiss, "From learning models of natural image patches to whole image restoration", Computer Vision (ICCV), 2011 IEEE International Congerence on, 2011, pp. 479-486.

D. Zoran and Y. Weiss, "Natural images, Gaussian mixtures and dead leaves", Neural Information Processing Systems (NIPS), 2012.

R. Salakhutdinov and G. Hinton, "An efficient learning procedure for deep Boltzman machines", Neural Computation, vol. 24, No. 8, pp. 1967-2006, 2012.

G. Yu, G. Sapiro, S. Mallat, "Solving inverse problems with piecewise linear estimators: from Gaussian mixture models to structured sparsity", IEEE Transaction on Image Processing, vol. 21, No. 5, pp. 2481-2499, 2012.

Y. Q. Wang, J.-M. Morel, "SURE guided Gaussian mixture image denoising", SIAM Journal on Imaging Sciences, vol. 6, No. 2, pp. 999-1034, 2013.

Y. Chen, Y. Li, W. Yu, L. Luo, W. Chen, C. Toumoulin, "Joint-MAP tomographic reconstruction with patch similarity based mixture prior model", Multiscale Modeling and Simulation, vol. 9, No. 4, pp. 1399-1419, 2011.

\* cited by examiner

METHODS AND SYSTEMS FOR PERFORMING MODEL-BASED IMAGE PROCESSING

BACKGROUND OF THE INVENTION

The subject matter disclosed herein relates generally to imaging systems and more particularly, to methods and systems for performing model-based iterative reconstruction of images acquired from a computed tomography (CT) imaging system.

Traditionally, images have been reconstructed from Computed Tomography (CT) data using direct reconstruction algorithms such as filtered backprojection. Recently, model based iterative reconstruction (MBIR) algorithms have been utilized to reconstruct CT images. For example, in applications such as dual energy CT reconstruction, the reconstructed image corresponds to the decomposition of the object into material components, wherein each specific material has its own distinctive spatial structure, texture, and distribution.

Markov random fields (MRFs) have been used in MBIR algorithms for tomographic image reconstruction. MRFs provide a simple and generally effective method to model the spatial texture in the images. In operation, MRFs are used to model the spatial texture of an image by calculating a gradient between each pixel in the image and the neighbors surrounding the pixels. However, MRFs are not enabled to model properties of the image that correspond to the actual values of the pixel. More specifically, MRFs do not model pixel density values that are based on the actual value or magnitude of the pixels. Rather, MRF models, model the pixels based on the local gradient between the pixel and their neighbors. As a result, it may be difficult to distinguish the various material components in the image. For example, the pixel intensity values are generated based on Hounsfield units. Different Hounsfield units are assigned to each pixel based on the property of the materials being images. Accordingly, it may be difficult to distinguish materials such as bones from other materials such as soft tissue when designing MRF models. Moreover, it is often difficult to estimate the various parameters utilized in the MRFs. As a result, the MRFs are less effective in capturing the subtle characteristics of complex images.

BRIEF DESCRIPTION OF THE INVENTION

In one embodiment, a method of generating a model for image processing is provided. The method includes selecting at least one reference image from a plurality of reference images, partitioning the at least one reference image into a plurality of patches, generating a probability distribution for each of the patches, and generating a model of a probability distribution for the at least one reference image using the probability distributions for each of the patches.

In another embodiment, a non-transitory computer readable medium is provided. The non-transitory computer readable medium is programmed to instruct a computer of a Computed Tomography (CT) system to receive a user input selecting at least one reference image from a plurality of reference images, automatically partition the at least one reference image into a plurality of patches, and generate a probability distribution for each of the patches. The computer readable medium is also programmed to generate a model of a probability distribution for the at least one reference image using the probability distributions for each of the patches.

In a further embodiment, a computed tomography (CT) imaging system is provided. The CT imaging system includes a detector configured to output x-ray attenuation information and a processor coupled to the detector. The processor is configured to receive the x-ray attenuation information and receive a user input selecting at least one reference image from a plurality of reference images, automatically partition the at least one reference image into a plurality of patches, and generate a probability distribution for each of the patches. The processor is further configured to generate a model of a probability distribution for the at least one reference image using the probability distributions for each of the patches.

DETAILED DESCRIPTION OF THE INVENTION

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry or software components. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the term "reconstructing" or "rendering" an image or data set is not intended to exclude embodiments in which data representing an image is generated, but a viewable image is not. Therefore, as used herein the term "image" broadly refers to both viewable images and data representing a viewable image. However, many embodiments generate, or are configured to generate, at least one viewable image.

Various embodiments provide systems and methods for generating a model which may be used to reconstruct computed tomographic (CT) images. In general, the model is embodied as a Gaussian Mixture Markov Random Fields (GM-MRF) model that is configured to model the density of the pixels and also concurrently model the spatial structure of the pixels. For example, in operation a reference image is selected. The reference image includes a plurality of pixels. A patch is generated for each of the plurality of pixels in the reference image. A probability distribution is calculated for each individual patch. The probability distributions for the plurality of patches are then combined by taking the geometric mean to form a single probability distribution model for the reference image.

Thus, in operation the GM-MRF model is configured to generate a plurality of individual patch models by jointly modeling the patch density and the spatial structure and texture of each patch, which is of particular importance for applications such as single and dual energy CT reconstruction. More specifically, each of the mixture components of the GM-MRF model specifies the mean of a particular patch, which in general corresponds to a particular material having a distinctive spatial structure in the CT images. Moreover, each of the mixture components of the GM-MRF model also specifies an inverse covariance for the patch, which provides information that reflects the particular statistical behavior of each patch because the eigenvalues of the inverse covariance are inversely proportional to the variances of the corresponding elements in the mixture component. During image reconstruction, the GM-MRF model can be used to control the regularization for the particular patch. Additionally, the GM-MRF model includes easily estimated parameters that are generated by merging the local patch models. More specifically, the GM-MRF model has an exact parameter, which provides information on a quantity of possible filings of the plane given the patch formulation in order to maintain the same energy after merging from the local patch models. In operation, the parameters of the GM-MRF model may be estimated using, for example, Gaussian mixture parameter estimation, which enables accurate modeling of the local patches with expressive Gaussian mixture model, while the parameter estimation is still computationally tractable. In various embodiments, the GM-MRF model also provides a framework for computing maximum a posteriori (MAP) estimates that are based on majorization-minimization using surrogate functions. Construction of exact surrogate functions for the energy function results in a sequence of quadratic optimizations, which makes the solution computationally tractable.

Figure 1:
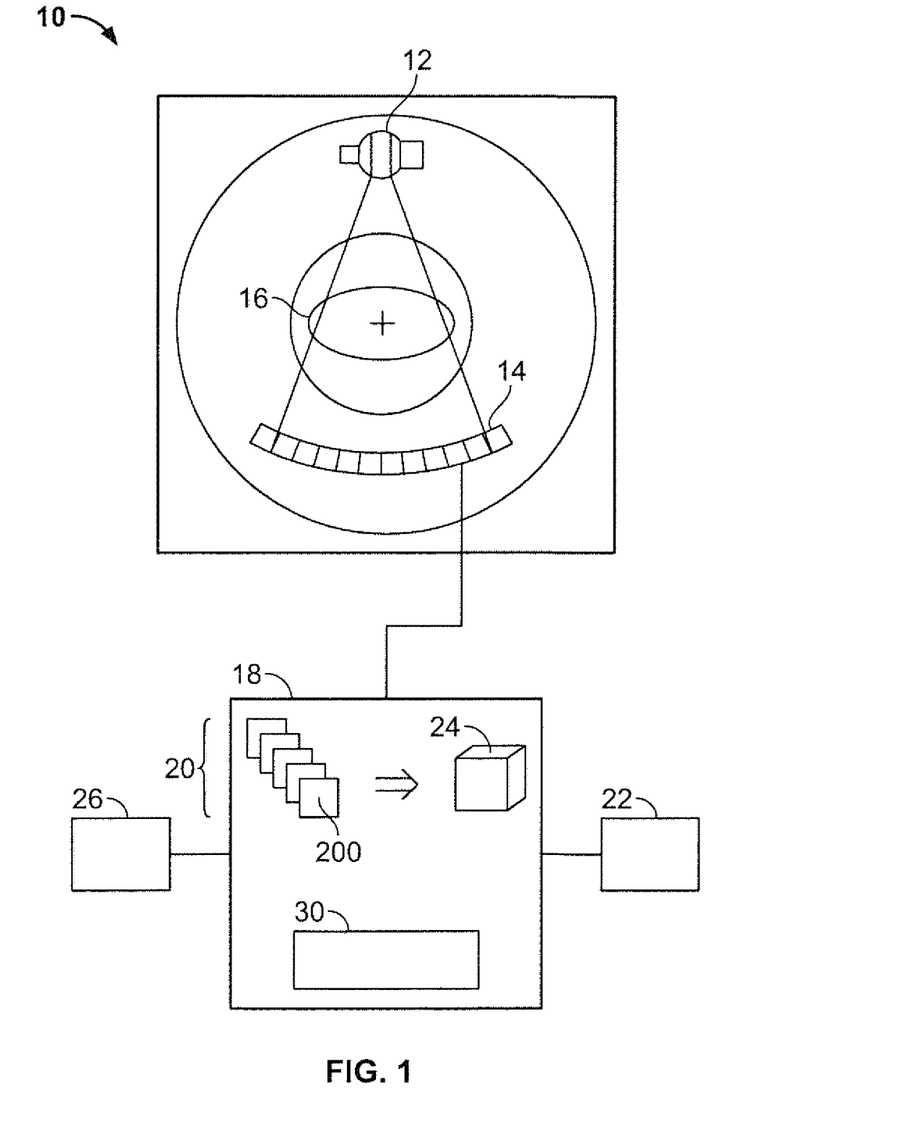
FIG. 1 is a simplified block diagram of an imaging system formed in accordance with various embodiments.

FIG. 1 illustrates a simplified block diagram of an exemplary imaging system 10 that is formed in accordance with various embodiments. The imaging system 10 may be embodied as a dual-energy CT imaging system, a single energy CT imaging system, or any other type of imaging system. The imaging system 10 includes an x-ray source 12 and a detector 14 that are used to scan a subject 16. A computer 18 processes the acquired information received from the detector 14 and prepares a plurality of two-dimensional (2D) images 20 that may be displayed on a display 22. It should be realized that any quantity of 2D images 20 may be displayed on the display 22. In the exemplary embodiment, each of the 2D images 20 represents a slice through a 3D volume dataset 24 at a specific location, or a volume rendering. The 3D volume dataset 24 may be displayed concurrently with or separately from the 2D images 20. The imaging system 10 also includes a model generating module 30 that is programmed to automatically generate a model for reconstructing the images 20 as is described in more detail below. In some embodiments, the model generating module 30 may be formed as part of the computer 18 as shown in FIG. 1. Optionally, the model generating module 30 may be formed separately from the computer 18.

The model generating module 30 is configured to implement various methods described herein. The model generating module 30 may be implemented as a piece of hardware that is installed in the computer 40. Optionally, the model generating module 30 may be implemented as a set of instructions that are installed on the computer 18. The set of instructions may be stand alone programs, may be incorporated as subroutines in an operating system installed on the computer 18, may be functions in an installed software package on the computer 18, and the like. It should be understood that the various embodiments are not limited to the arrangements and instrumentality shown in the drawings.

The imaging system 10 also includes a user interface 26 that allows an operator to enter data, enter and change scanning parameters, access protocols, measure structures of interest, and the like. The user interface 26 also enables the operator to transmit and receive information to and/or from the processor 18 and/or the module 30 that instructs the processor 18 and/or the module 30 to perform the various methods described herein.

Figure 2:
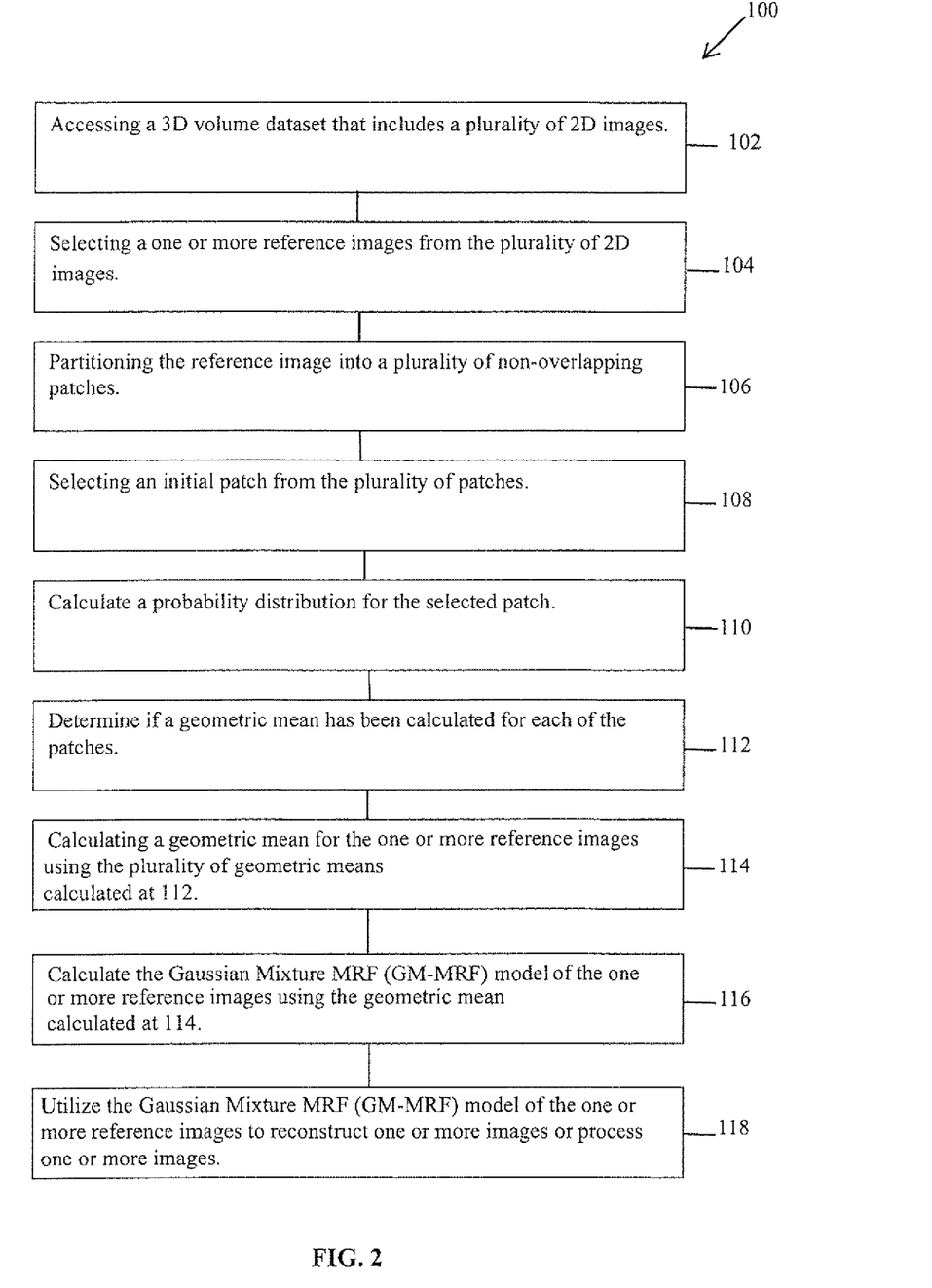
FIG. 2 is a flowchart illustrating a method of generating a model for reconstructing a plurality of images in accordance with various embodiments.

FIG. 2 is a flowchart illustrating a method 100 for generating a model for reconstructing an image. In various embodiments, the method 100 may be implemented using either the processor 18 or the module 30 both shown in FIG. 1. It should be noted that although the method 100 is described in connection with a CT imaging system having particular characteristics, such as the CT imaging system 10 shown in FIG. 1, the various embodiments described herein are not limited to CT imaging or to any particular imaging characteristics. For example, although the method 100 is described in connection with images acquired using a dual-energy CT imaging system as shown in FIG. 1, the method 100 may also be utilized to model images acquired using a single energy CT imaging system or any other type of imaging system.

The method 100 includes accessing at 102 with a processor, such as the processor 18 shown in FIG. 1, a 3D volume dataset, such as the 3D volume dataset 24, also shown in FIG. 1. In the exemplary embodiment, the 3D volume dataset 24 includes a sequence of N two-dimensional (2D) images 20 of the subject 16. In one embodiment, the 3D volume dataset 24 may include grayscale data, scalar grayscale data, parameters or components such as color, displacement, velocity, temperature, density, concentration, material strain or other information or source of information that may be coded into an image. The 2D images 20 may be acquired over the duration of a patient scan, for example. The quantity of 2D images 20 may vary from patient to patient and may depend upon the length of the individual patient's scan as well as the flame rate of the imaging system 10.

In the exemplary embodiment, the 2D images 20 are acquired sequentially during a single scanning procedure. Therefore, the 2D images 20 are of the same subject or patient 16, but acquired at different times during the same scanning procedure. Thus, in the exemplary embodiment, the plurality of 2D images 20 includes images acquired at different time periods during the scanning procedure. It should therefore be realized that in the exemplary embodiment, the 3D volume dataset 24 includes more than the two 2D images 20.

Figure 3:
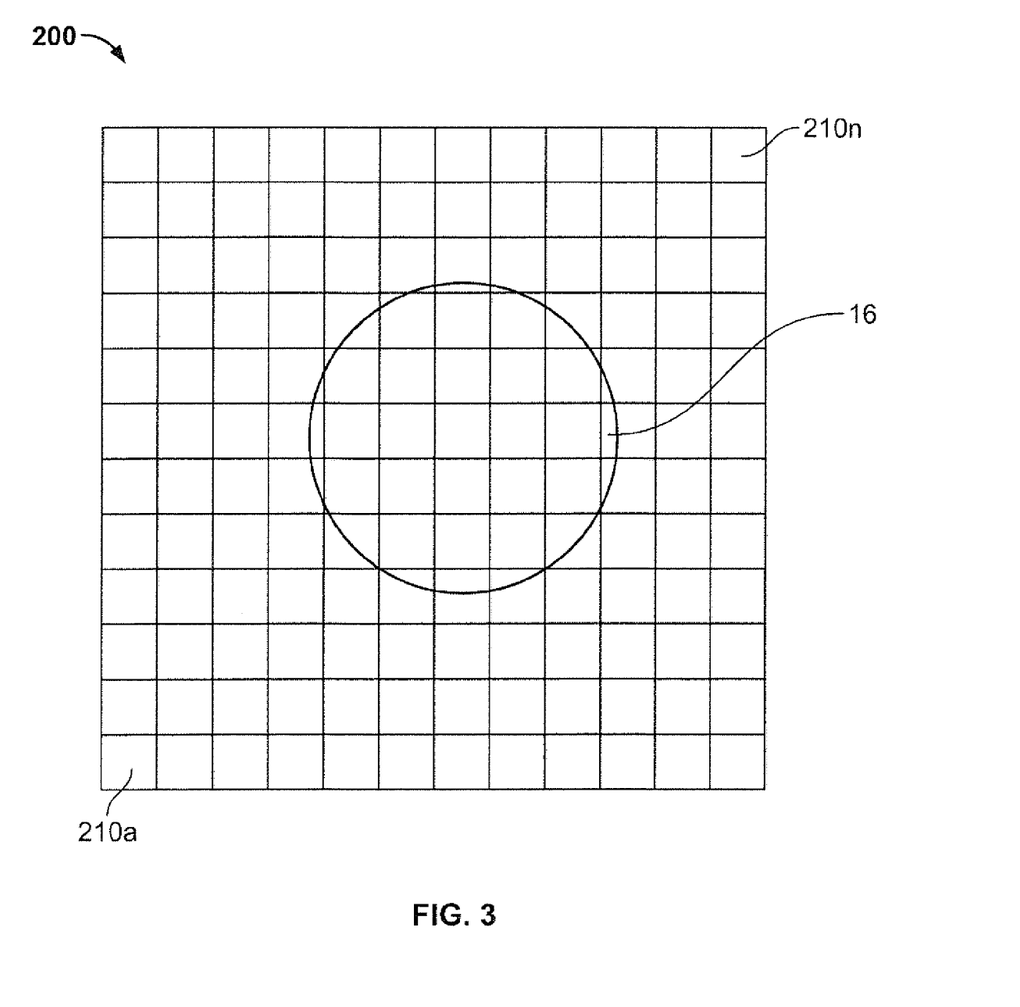
FIG. 3 is a reference image that may be selected in accordance with various embodiments.

At 104 one or more reference images 200 are selected from the plurality of reconstructed images 20. In some embodiments, a volume of images (e.g., 3D volume) may be selected. FIG. 3 illustrates the exemplary reference image 200 that may be selected at 104. It should be realized that any one or more of the 2D images 20 may be selected as the reference image 200. As shown in FIG. 3, the reference image 200 is formed from a plurality of pixels labeled 210a . . . 210n.

Figure 4:
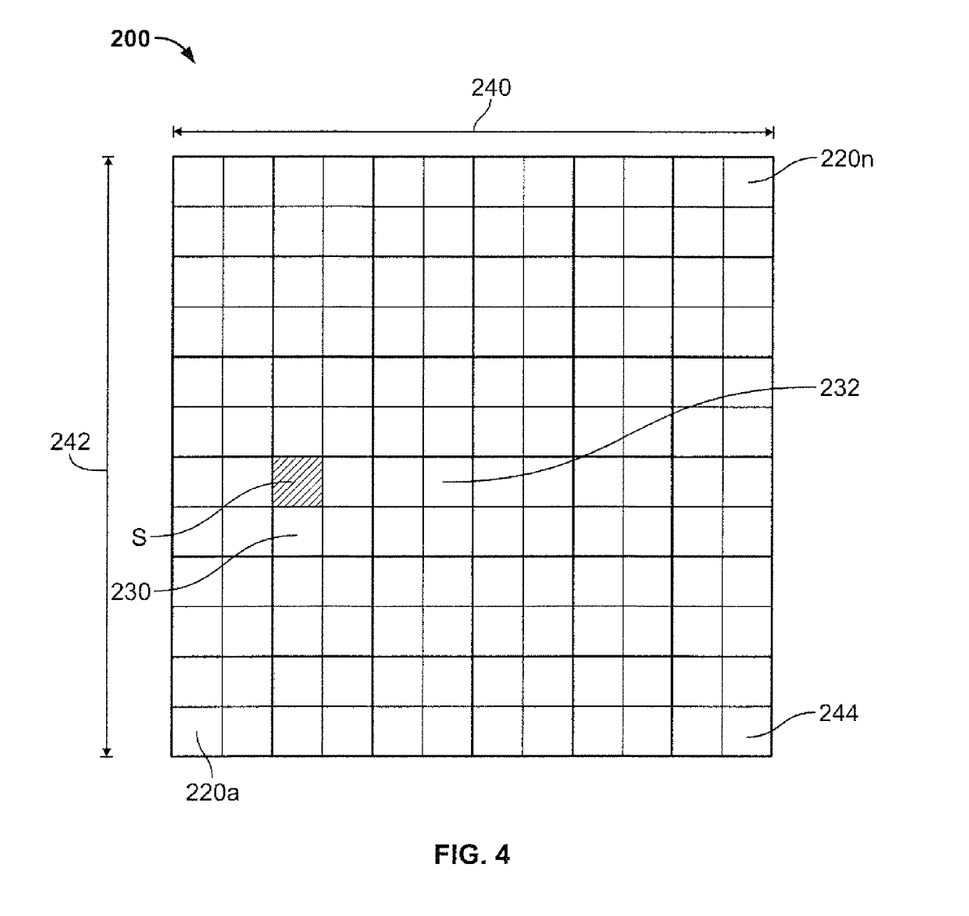
FIG. 4 illustrates a plurality of patches that may be formed in accordance with various embodiments.

At 106, the reference image 200 is partitioned or divided into a plurality of non-overlapping blocks or patches 220a . . . 220n, respectively, as shown in FIG. 4 that cover a plane of the reference image 200. As used herein, the term "tile" refers to a single patch 220. Additionally, the term "tiling" refers to partitioning the reference image 200 such that the plurality of patches 220 or tiles, are arranged in a pattern on the reference image 200 to form an array of patches 220 that is analogous to floor tiles.

For example, as shown in FIG. 4, the reference image 200 has a width 240 and a length 242 that define a plane 244 of the reference image 200. In the illustrated embodiment, each of the patches 220 is sized as a square 2×2 matrix of pixels 210. More specifically, in the illustrated embodiment, each of the patches 220a . . . 220n is formed as a 2×2 matrix that includes four adjacent pixels 210. Therefore, in the illustrated embodiment, the plane 244 of the reference image 200 is covered with an array of patches 220, wherein each patch 220 includes four pixels. However, it should be realized that although FIG. 4 illustrates the reference image 200 being partitioned into an array of 2×2 patches 220 that cover the plane 244, the reference image 200 may be partitioned into patches of any size and shape. For example, each of the patches 220 may be formed as a 3×3 patch such that the plane 244 of the reference image 200 is covered by an array of patches, wherein each patch 220 includes nine pixels. In various embodiments, each of the patches 220 may be formed as a 3×4 patch, a 4×4 patch, a 4×5 patch, a 5×5 patch, etc. It should be appreciated that different dimensions of patch sizes may be provided. In some embodiments, 3D patches may be provided, for example, a 2×2×2 patch, a 2×2×3 patch, a 2×3×3 patch, a 3×3×3 patch, etc. It should be noted that various embodiments may be applied to 2D image slices and/or 3D image volume (e.g., reconstruct an entire volume instead of generating slice by slice).

Referring again to FIG. 2, at 108 an initial patch is selected from the plurality of patches 220. For example, a patch 230, shown in FIG. 4 may be selected. At 110, a probability distribution is calculated for the selected patch 230. It should be realized that the term probability distribution may include a geometric mean, an inverse covariance matrix, and one or more parameters. Thus, in various embodiments, the following are calculated: a mean vector ($\mu$), an inverse covariance (B matrix), and one or more parameters (which in various embodiments is the sum of a combination of parameters, or which in various embodiment is the mixture probability parameter ($\pi$)).

For example, let x be the reference image 200 with pixels s$\in$S, where S is the set of all pixels 210 in the reference image 200. Moreover, let $z_s$ be a patch, such as the patch 230 in the reference image 200 with the pixel s at the upper left corner. Thus, the patch $z_s$ may be defined as $z_s = \{x_r : r \in s+W\}$ where W is a window of p pixels which is the illustrated embodiment is four pixels 210.

For example, as described above each of the patches 220 are arranged adjacent to each other such that the patches abut against each other in a non-overlapping pattern. Optionally, the patches may partially overlap each other. Accordingly, each patch, such as the patch 230, may be modeled as having a multivariate Gaussian mixture distribution with K subclasses in accordance with:

$$g(z_s) = \sum_{k=0}^{K-1} \pi_k \frac{1}{(2\pi)^p} |B_k|^{\frac{1}{2}} \exp\left\{-\frac{1}{2}\|z_s - \mu_k\|\frac{2}{B_k}\right\} \quad \text{Equation 1}$$

where the parameters $\pi k$, $\mu k$, Bk represent the mixture probability, mean, and inverse covariance of the subclass k, respectively. Moreover, assume that S0, . . . , S$\eta$−1 is a set of all pixels within the patch 230 after being partitioned into $\eta$ sets, wherein each of the $\eta$ sets cover the plane 244 of the image 200. More specifically, assume that $\{z_s\}$, s$\in$Sm includes all the pixels in x. For example, in one embodiment each zs may be a square patch formed as an M×M matrix of pixels and the set of patches $\{z_s\}$, s$\in$Sm tile the plane 244. Accordingly, in operation to generate the multivariate Gaussian mixture distribution of the patch 230, the patch 230 is shifted in the X and Y positions. Thus, any set of patches 230 may be used to encompass or tile the image plane (2D) or image volume (3D) or any set of shifted patches may be used to encompass or tile the image plane (2D) or image volume (3D). It should be noted that different patch tiling with the same patch size or different patch size may be used. For example, $\eta$ defines the number of different possibilities and the patch 230 may be shifted in different directions. For example, for a 2×2 patch, the patch may be shifted by half a tile (or patch dimension) up, down, left, and/or right as viewed in FIGS. 5A-5D described below.

Thus, in some embodiments, the methods described herein may be utilized to generate a global image model that may be utilized to reconstruct a variety of images. As used herein, the term global image model refers to a prior model that may be utilized to reconstruct or process a variety of images. To generate the global image model, the image is partitioned into a plurality of patches that tile the plane in a first arrangement. For example, and referring again to FIG. 4, it should be realized that the reference image 200 may be partitioned into various arrangements of patches. For an array of 2×2 patches there are four distinct tiling arrangements that may be used to partition the reference image 200. For example, the array of patches may be shifted side-to-side in the X-direction or shifted up and/or down in the Y-direction. Accordingly, to generate the prior global model, a prior model, such as the GM-MRF model is generated for each of the tiling arrangements. In this example, four GM-MRF models are generated. The global model is then generated by calculating the geometric average of the distributions of all possible filings, which in this case are four possible filings. Thus, in this embodiment, the prior global model is generated by calculating a geometric average for each of the filings, and then calculating a geometric average using the four geometric averages calculated for each possible tiling. In some embodiments the geometric mean of all possible filings may be used to improve modeling.

Figure 5A:
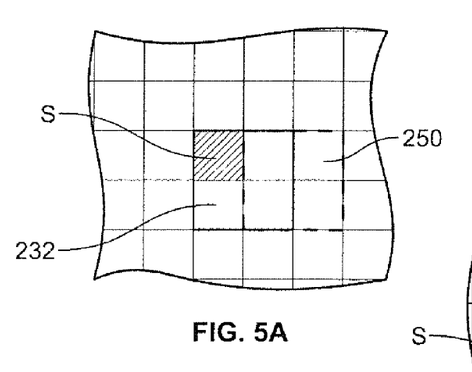
FIGS. 5A-5D illustrate a method of calculating a geometric mean for a single patch in accordance with various embodiments.
Figure 5B:
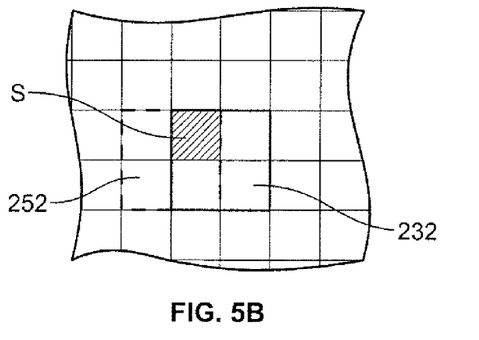
Figure 5C:
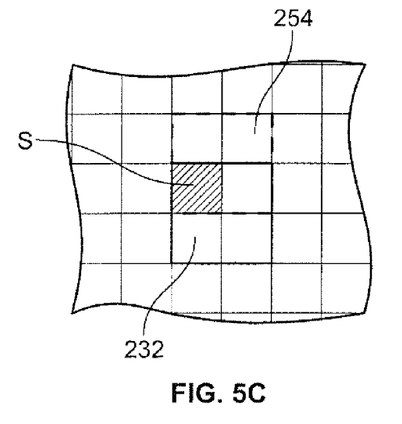
Figure 5D:
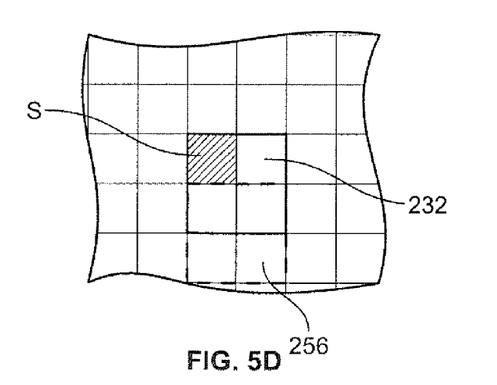

For example, FIG. 5A illustrates the patch 230 shifted along an X-axis in a first direction to define a first non-local patch 250. FIG. 5B illustrates the patch 230 shifted along the X-axis in a second direction to define a second non-local patch 252. FIG. 5C illustrates the patch 230 shifted along a Y-axis in a first direction to define a third non-local patch 254. FIG. 5D illustrates the patch 230 shifted along the Y-axis in a second direction to define a fourth non-local patch 256. Accordingly, the Gaussian mixture distribution is calculated for the patch 230 at the four different positions, shown in FIGS. 5A-5D in accordance with Equation 1. More specifically, a Gaussian probability distribution is calculated for the first non-local patch 250, the second non-local patch 252, the third non-local patch 254, and the fourth non-local patch 256. The geometric mean for the Gaussian mixture distributions patch 230 is then calculated in accordance with Equation 1. It should be noted that in various embodiments, the modeling of the patches and patch distribution includes the calculation of the mean, but also the inverse covariance and the mixture probability parameter as described herein (and as illustrated in FIG. 1). Thus, in various embodiments, all of these components are calculated from the one or more reference images in order to form one or more models (e.g., GM-MRF model).

Moreover, the distribution of the all the patches 220 forming the reference image 200 may be modeled as the product of the distribution for each patch in accordance with:

$$Pm(x) = \prod_{s \in S_m} g(z_s) = \exp\left\{-\sum_{s \in S_m} V(z_s)\right\} \quad \text{Equation 2}$$

where $V(z_s) = -\log\{g(z_s)\}$. In this case, $p_m(x)$ is a proper distribution that has the desired distribution for each patch 220.

Referring again to FIG. 2, in various embodiments, steps 108 and 110 are iteratively repeated for each of the patches 220. For example, a subsequent patch 232 may be selected 108 as shown in FIG. 4. The mean, an inverse covariance matrix, and/or one or more parameters of the patch 232 are then calculated in accordance with Equations 1 and 2 as described above with respect to the patch 230. Thus, at 112 the module 30 determines whether a mean has been calculated for each of the patches 220. Accordingly, steps 108 and 110 are iteratively repeated until a mean is calculated for each of the patches 220 forming the reference image 200.

In operation, the discrete tiling of the plane, i.e. the reference image 200, may introduce artificial boundaries between the non-overlapping patches 220. For example, because the plane 244 of the reference image 200 is tiled with a plurality of non-overlapping patches 220, the boundaries between the patches 220 may result in artifacts that may reduce the texture quality of the reconstructed image. Accordingly, in various embodiments, to remove potential artifacts that may occur between the boundaries defined between the separate patches 220, and thus improve the texture of the reference image 200, the method 100 further includes calculating at 114 the geometric mean of each of the possible tilings for the reference image 200 to determine the following distribution:

$$p(x) = \frac{1}{z}\left(\prod_{m=0}^{n-1} P_m(x)\right)^{1/n} = \frac{1}{z}\exp\left\{-\frac{1}{\eta}\sum_{s \in S} V(z_s)\right\} \quad \text{Equation 3}$$

where the normalizing constant z is utilized to assure that $p(x)$ is a proper distribution after the geometric mean is computed using Equation 1. It should be realized that the term $\eta$ is equivalent to the quantity of pixels forming the patch 230. For example, in the illustrated embodiment, the patch 230 is formed as a 2×2 matrix of pixels. Accordingly, in the illustrated embodiment, $\eta=4$. In another embodiment, the patch 230 may be formed as a 3×3 matrix of pixels. Accordingly, in this embodiment, $\eta=9$, etc. It should be noted that in a 3D case, such as if the patch 230 is formed from a 3×3×3 matrix or pixels then $\eta=27$.

Referring again to FIG. 2, at 116, the Gaussian Mixture MRF (GM-MRF) model of the reference image 200 may be calculated in accordance with:

$$V(z_s) = -\log\left\{\sum_{k=0}^{K-1} \pi_k \frac{1}{(2\pi)^p} |B_k|^{\frac{1}{2}} \exp\left\{-\frac{\|z_s - \mu_k\|_{B_k}^2}{2}\right\}\right\} \quad \text{Equation 4}$$

Thus, the steps 102-116 generate one or more models (e.g., GM-MRF model) that may be used subsequently used as described herein. The steps 102-116 in various embodiments define a training process or method that that is performed on the reference image(s) (or reference volume) to generate the one or more models. For example, the steps 102-116 in various embodiment train the parameters (e.g., define the parameters) for use in image reconstruction or image processing.

At 118, the GM-MRF model calculated at 116 is utilized to process or reconstruct one or more images or is applied to one or more images. Thus, the reference image(s) are used to generate, for example, the GM-MRF model, which is then used on other sets of data. For example, the GM-MRF model may be used in an image reconstruction process wherein image reconstruction of scan data or raw data (projection views) is performed. As another example, the GM-MRF model may be used for image processing, such as applying the GM-MRF model to one or more images (different than the reference images), such as for de-noising or for resolution improvement (e.g., removing image noise, or increasing image edge sharpness).

In various embodiments, for example, the GM-MRF model calculated at 116 may be utilized to calculate maximum a posteriori (MAP) estimates that are used to perform image reconstruction at 118. To make the computation tractable, MAP reconstruction of images can be based on majorization-minimization using surrogate functions as explained in more detail below. In operation, construction of exact surrogate functions for the energy function result in a sequence of quadratic optimizations which enable the solution of the MAP function to be performed relatively easily.

In various embodiments, the MAP estimate of the GM-MRF model calculated at 116 may be calculated in accordance with:

$$\hat{x} \leftarrow \underset{x}{\operatorname{argmin}}\left\{-\log p(y|x) + \frac{1}{\eta}\sum_{s \in S} V(z_s)\right\} \quad \text{Equation 5}$$

where the parameters $\pi_k$, $\mu_k$, $B_k$ for each subclass k in Equation 1 may be estimated using a conventional expectation maximization (EM) algorithm and V is the image volume. It should be noted that the MAP estimate is part of a training process or procedure described above.

In some embodiments, it may be difficult to calculate a direct optimization for the second term in Equation 5. Accordingly, in some embodiments, the second term in Equation 5 may be replaced with more computationally efficient function that is formed using a mixture of quadratic functions.

For example, for the function $$u(x) = \frac{1}{\eta} \sum_{s \in S} V(z_s) \qquad \text{Equation 6}$$

where $V(z_s)$ is defined by Equation 4, a quadratic function may be defined in accordance with:

$$u(x; x') = \frac{1}{2\eta} \sum_{s \in S} \sum_{k=0}^{K-1} \tilde{w}_k \|z_s - \mu_k\|_{B_k}^2 + c(x') \qquad \text{Equation 7}$$

where x' represents the current state of the image, and $$\tilde{w}_k = \frac{\pi_k |B_k|^{\frac{1}{2}} \exp\left\{-\frac{1}{2}\|z'_s - \mu_k\|_{B_k}^2\right\}}{\sum_{j=0}^{K-1} \pi_j |B_j|^{\frac{1}{2}} \exp\left\{-\frac{1}{2}\|z'_s - \mu_j\|_{B_j}^2\right\}} \qquad \text{Equation 8}$$

$$c(x') = \frac{1}{\eta} \sum_{s \in S} \left\{ V(z'_s) - \frac{1}{2} \sum_{k=0}^{K-1} \tilde{w}_k \|z'_s - \mu_k\|_{B_k}^2 \right\} \qquad \text{Equation 9}$$

wherein $z'_s$ represents a patch in x'. Accordingly, by utilizing an exemplary lemma, it may be shown that:

$$u(x'; x') = u(x) \qquad \text{Equation 10}$$
$$u(x; x') \geq u(x) \qquad \text{Equation 11}$$

Thus, Equations 10 and 11 illustrate that u(x; x') is a surrogate function for u(x) such that majorization-minimization methods may be utilized and a reduction of u(x; x') ensures an equivalent reduction of u(x).

As described above, a lemma may be utilized to define surrogate functions for logs of the exponential mixtures. In various embodiments, one exemplary lemma that may be utilized as described above is defined as $$f(x) = \sum_k w_k \exp\{-v_k(x)\} \qquad \text{Equation 12}$$

$$q(x; x') \triangleq -\log f(x') + \sum_k \tilde{\pi}_k (v_k(x) - v_k(x')) \qquad \text{Equation 13}$$

$$q(x'; x') = -\log f(x') \qquad \text{Equation 14}$$

$$q(x; x') \geq -\log f(x) \qquad \text{Equation 15}$$

Therefore, any optimization problem in the form:

$$\hat{x} \leftarrow \operatorname*{argmin}_{x} \{f(x) + u(x)\} \qquad \text{Equation 16}$$

can be implemented as a sequence of optimizations as:

$$\operatorname{repeat}\left\{\hat{x} \leftarrow \operatorname*{argmin}_{x}\{f(x) + u(x; x')\} x' \leftarrow \hat{x}\right\} \qquad \text{Equation 17}$$

where an optimization problem with quadratic priors is solved at each iteration.

The various methods described herein provide a method of modeling the statistical behavior of images. In one embodiment, the statistical behavior is modeled using a multivariate distribution of patches of pixels formed in the image. Using a multivariate distribution of patches of pixels enables the model to reconstruct images that include different gray levels which represent different materials, such as air, bone, and/or soft tissue, which have different statistical behavior spatially. Therefore, in operation, the methods described herein model both the spatial distribution and the density together as a single multivariate distribution. In dual energy systems, this may be referred to herein as material decomposition because different materials have different signatures and behave differently.

In various embodiments, the models described herein are utilized to reconstruct or generally process CT images. Thus, the model provides useful information as to the distribution of the image that corresponds to the CT data. The model also functions to sharpen the various features in the images by utilizing a statistical representation of the image.

More specifically, consider a partial image, e.g. a single pixel, then consider the relationship between the pixel and some of its neighbors. In one embodiment, a method of describing this relationship is a Markov random field (MRF). However, as described above the conventional MRF does not model the properties of the image that correspond to the actual values of the pixel to be modeled. Conventional MRF models only model pixel-wise differences in the image. Whereas various methods described herein model the differences between patch density and spatial structure and texture among patches. More specifically, the image is partially modeled based on the actual value or magnitude of the pixels by modeling the distribution of the gray level in the patches and also the texture in the patches. Therefore, in various aspects, the GM-MRF model is an embodiment of a model that includes more information than a conventional MRF model.

Figure 6:
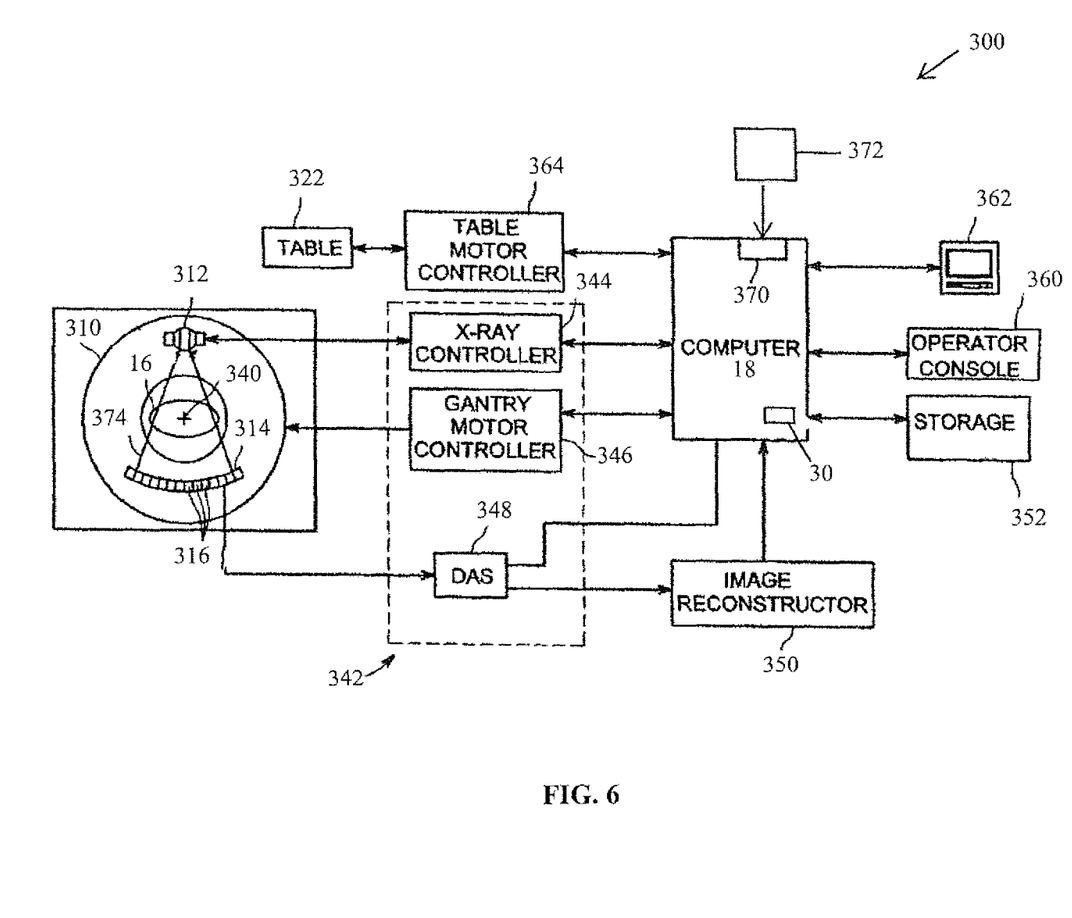
FIG. 6 is a pictorial view of an exemplary imaging system formed in accordance with various embodiments.

The various methods described herein may be implemented using a medical imaging system. For example, FIG. 6 is a block schematic diagram of an exemplary CT imaging system 300 that may be utilized to perform the methods described herein. Although the CT imaging system 300 is illustrated as a standalone imaging system, it should be realized that the CT imaging system 300 may form part of a multi-modality imaging system. For example, the multi-modality imaging system may include the CT imaging system 300 and a positron emission tomography (PET) imaging system, or a single photon emission computed tomography (SPECT) imaging system. It should also be understood that other imaging systems capable of performing the functions described herein are contemplated as being used.

The CT imaging system 300 includes a gantry 310 that has the X-ray source 312 that projects a beam of X-rays toward the detector array 314 on the opposite side of the gantry 310. The detector array 314 includes a plurality of detector elements 316 that are arranged in rows and channels that together sense the projected X-rays that pass through a subject, such as the subject 16 shown in FIG. 1. The imaging system 300 also includes the computer 18 that receives the projection data from the detector array 314 and processes the projection data to reconstruct an image of the subject 16. In operation, operator supplied commands and parameters are used by the computer 18 to provide control signals and information to reposition a motorized table 322. More specifically, the motorized table 322 is utilized to move the subject 16 into and out of the gantry 310. Particularly, the table 322 moves at least a portion of the subject 16 through a gantry opening (not shown) that extends through the gantry 310.

As discussed above, the detector 314 includes a plurality of detector elements 316. Each detector element 316 produces an electrical signal, or output, that represents the intensity of an impinging X-ray beam and hence allows estimation of the attenuation of the beam as it passes through the subject 16. During a scan to acquire the X-ray projection data, the gantry 310 and the components mounted thereon rotate about a center of rotation 340. FIG. 6 shows only a single row of detector elements 316 (i.e., a detector row). However, the multislice detector array 314 includes a plurality of parallel detector rows of detector elements 316 such that projection data corresponding to a plurality of slices can be acquired simultaneously during a scan.

Rotation of the gantry 310 and the operation of the X-ray source 312 are governed by a control mechanism 342. The control mechanism 342 includes an X-ray controller 344 that provides power and timing signals to the X-ray source 312 and a gantry motor controller 346 that controls the rotational speed and position of the gantry 310. A data acquisition system (DAS) 348 in the control mechanism 342 samples analog data from detector elements 316 and converts the data to digital signals for subsequent processing. For example, the subsequent processing may include utilizing the model generating module 30 to implement the various methods described herein. An image reconstructor 350 receives the sampled and digitized X-ray data from the DAS 348 and performs high-speed image reconstruction. The reconstructed images are input to the computer 18 that stores the image in a storage device 352. Optionally, the computer 18 may receive the sampled and digitized X-ray data from the DAS 348 and perform various methods described herein using the module 30. The computer 18 also receives commands and scanning parameters from an operator via a console 360 that has a keyboard. An associated visual display unit 362 allows the operator to observe the reconstructed image and other data from computer.

The operator supplied commands and parameters are used by the computer to provide control signals and information to the DAS 348, the X-ray controller 344 and the gantry motor controller 346. In addition, the computer 18 operates a table motor controller 364 that controls the motorized table 322 to position the subject 16 in the gantry 310. Particularly, the table 322 moves at least a portion of the subject 16 through the gantry opening.

In various embodiments, the computer 18 includes a device 370, for example, a floppy disk drive, CD-ROM drive, DVD drive, magnetic optical disk (MOD) device, or any other digital device including a network connecting device such as an Ethernet device for reading instructions and/or data from a tangible non-transitory computer-readable medium 372, that excludes signals, such as a floppy disk, a CD-ROM, a DVD or another digital source such as a network or the Internet, as well as yet to be developed digital means. In another embodiment, the computer 18 executes instructions stored in firmware (not shown). The computer 18 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the X-ray source 312 and the detector array 314 are rotated with the gantry 310 within the imaging plane and around the subject 16 to be imaged such that the angle at which an X-ray beam 374 intersects the subject 16 constantly changes. A group of X-ray attenuation measurements, i.e., projection data, from the detector array 314 at one gantry angle is referred to as a "view". A "scan" of the subject 16 comprises a set of views made at different gantry angles, or view angles, during one revolution of the X-ray source 312 and the detector 314. In a CT scan, the projection data is processed to reconstruct an image that corresponds to a three-dimensional volume taken of the subject 16.

Exemplary embodiments of a multi-modality imaging system are described above in detail. The multi-modality imaging system components illustrated are not limited to the specific embodiments described herein, but rather, components of each multi-modality imaging system may be utilized independently and separately from other components described herein. For example, the multi-modality imaging system components described above may also be used in combination with other imaging systems.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments, Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc., are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method of generating a model for image processing, said method comprising:
   selecting at least one reference image from a plurality of reference images; partitioning the at least one reference image into a plurality of patches;
   generating an individual patch model for each of the patches, wherein the individual patch model for each patch jointly models a patch density along with spatial structure and texture of the corresponding patch, wherein each individual patch model includes a mean of the corresponding patch and an inverse covariance of the corresponding patch; and
   generating a model of a probability distribution for the at least one reference image using the individual patch models for the patches; wherein generating the model comprises: calculating a density value for each of the patches; and
   merging the density values to generate a model of the reference image, the model including a texture and a density of the reference image.

2. The method of claim 1, further comprising reconstructing one or more images from raw data using the generated model, wherein the one or more images comprise at least one of a two-dimensional image or a three-dimensional image.

3. The method of claim 1, further comprising performing image processing on one or more images by applying the generated model to the one or more images.

4. The method of claim 1, wherein the selecting comprises selecting an image volume defined by at least some of the plurality of reference images.

5. The method of claim 1, further comprising modeling a multi-material density and a spatial texture of the reference image using the generated model.

6. The method of claim 5, further comprising modeling the multi-material density concurrently with the spatial texture.

7. The method of claim 1, wherein the model includes a joint model of a density and a texture of the reference image, the method further comprising:
   incorporating the joint model into a model based iterative reconstruction (MBIR) algorithm; and
   reconstructing the plurality of images using the incorporated model.

8. The method of claim 1, further comprising using a mixture distribution to model the probability distribution of the patches.

9. The method of claim 1, further comprising using a Gaussian mixture distribution to model the probability distribution of the patches.

10. A non-transitory computer readable medium programmed to instruct a computer of a Computed Tomography (CT) system to:
    receive a user input selecting at least one reference image from a plurality of reference images;
    automatically partition the at least one reference image into a plurality of patches; generate an individual patch model for each of the patches, wherein the individual patch model for each patch jointly models a patch density along with spatial structure and texture of the corresponding patch, wherein each individual patch model includes a mean of the corresponding patch and an inverse covariance of the corresponding patch; and
    generate a model of a probability distribution for the at least one reference image using the individual patch models for the patches; wherein generating the model comprises: calculating a density value for each of the patches; and
    merging the density values to generate a model of the reference image, the model including a texture and a density of the reference image.

11. The non-transitory computer readable medium of claim 10, being further programmed to reconstruct one or more images from raw data using the generated model, wherein the one or more images comprise at least one of a two-dimensional image or a three-dimensional image.

12. The non-transitory computer readable medium of claim 10, being further programmed to perform image processing on one or more images by applying the generated model to the one or more images.

13. The non-transitory computer readable medium of claim 10, being further programmed to model a multi-material density and a spatial texture of the reference image using the generated model.

14. The non-transitory computer readable medium of claim 10, being further programmed to model the multi-material density concurrently with the spatial texture.

15. The non-transitory computer readable medium of claim 10, wherein the model includes a joint model of a density and a texture of the reference image, the computer readable medium being further programmed to:
    incorporate the joint model into a model based iterative reconstruction (MBIR) algorithm; and
    reconstruct the plurality of images using the incorporated model.

16. The non-transitory computer readable medium of claim 10, being further programmed to use a mixture distribution to model the probability distribution of the patches.

17. The non-transitory computer readable medium of claim 10, being further programmed to use a Gaussian mixture distribution to model the probability distribution of the patches.

18. A computed tomography (CT) imaging system comprising: a detector configured to output x-ray attenuation information; and a processor coupled to the detector, the processor being configured to:
    receive a user input selecting at least one reference image from a plurality of reference images;
    automatically partition the at least one reference image into a plurality of patches; generate an individual patch model for each of the patches, wherein the individual patch model for each patch jointly models a patch density along with spatial structure and texture of the corresponding patch, wherein each individual patch model includes a mean of the corresponding patch and an inverse covariance of the corresponding patch; and
    generate a model of a probability distribution for the at least one reference image using the individual patch models for the patches; wherein generating the model comprises: calculating a density value for each of the patches; and merging the density values to generate a model of the reference image, the model including a texture and a density of the reference image.

19. The CT system of claim 18, wherein the processor is further programmed to receive the x-ray attenuation information as raw data and reconstruct one or more images from the raw data using the generated model, wherein the one or more images comprise at least one of a two-dimensional image or a three-dimensional image.

20. The CT system of claim 18, wherein the processor is further programmed to perform image processing on one or more images reconstructed from the x-ray attenuation information by applying the generated model to the one or more images.

21. The CT system of claim 18, wherein the processor is further programmed to model a multi-material density and a spatial texture of the reference image using the generated model.

22. The CT system of claim 18, wherein the processor is further programmed to model the multi-material density concurrently with the spatial texture.

23. The CT system of claim 18, wherein the model includes a joint model of a density and a texture of the reference image, the processor is further programmed to:
  incorporate the joint model into a model based iterative reconstruction (MBIR) algorithm; and
  reconstruct the plurality of images using the incorporated model.

24. The CT system of claim 18, wherein the processor is further programmed to use a Gaussian mixture distribution to model the probability distribution of the patches.

* * * * *